US00PP10315P

United States Patent [19]

Sherman

[11] Patent Number: Plant 10,315

[45] Date of Patent: Apr. 7, 1998

[54] PEACH TREE 'UFGOLD'

[76] Inventor: Wayne B. Sherman, 2230 SW. 43 Pl., Gainsville, Fla. 32608

[21] Appl. No.: 716,930

[22] Filed: Sep. 10, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach tree which has a low winter chilling requirement of approximately 200 chill units (cu). The tree is of large size, is highly vigorous spreading growth habit and has showy pink flowers. Glands are reniform in shape and isolated to the basal portions of leaves. This tree, which has been denominated UFGold is a regular bearer of heavy crops of early maturing, large for early ripening season, with very firm non-melting flesh, clingstone fruit having yellow flesh color. Fruit is uniform, attractive, substantially symmetrical shape, and has an attractive normally 70 to 90% solid red over-color. The fruit ripens substantially with that of Flordaglo in early May at Gainesville, Fla.

2 Drawing Sheets

BACKGROUND OF THE NEW VARIETY

The present invention relates to a new and distinct variety of peach tree which is named UFGold and, more particularly to a peach tree which produces highly colored, good eating quality, clingstone, non-melting fruit which are mature for commercial shipment in early May at Gainesville and which are produced on a tree adapted to a mild winter climate. Asexual propagation was performed at Gainesville, Fla. where the selection was made and tested. Contrast is made to Flordaglo peach, a standard variety, for reliable description. This new variety is a promising candidate for commercial success in that it retains fruit firmness at the full flavor, tree ripe stage for 10 days on the tree.

ORIGIN OF THE VARIETY

This peach tree (genotype) originated in the tree fruit breeding program at the University of Florida, located at Gainesville, Fla. The seed parent was Fla. 84-18C (nonpatented), a non-melting flesh peach (originated as Diamante open-pollinated) and the pollen parent was Fla. 9-20C (nonpatented), a non-melting flesh peach (originated as shown in FIG. 1). UFGold peach was selected from about 100 sibs as the twenty fourth selection in 1990, exhibited yellow, non-melting clingstone flesh, and thus was designated Fla. 90-24C. It was propagated asexually as a uniform variety and determined at Gainesville to have unique tree and fruit characteristics making it worthy for commercial production. UFGold has transmitted uniformity through two successive standard asexual propagations by budding.

SUMMARY OF THE VARIETY

The new and distinct variety of peach tree bears yellow, non-melting flesh fruit, and has a low-chilling dormancy requirement. UFGold blooms with Flordaglo peach at Gainesville and is the only peach variety in the USA with such a low-chilling requirement that bears red skin, non-melting flesh, early-ripening, yellow flesh fruit. The estimated chilling requirement is 200 chill units. When grown in subtropical climates to take maximum advantage of its early bloom (low-chilling) UFGold will be among the first non-melting flesh peach varieties to ripen in the USA.

The present invention resulting in UFGold peach tree is characterized by non-melting flesh fruit of excellent flavor and eating quality on a tree adapted to mild winters. The trees are vigorous, productive and regular bearing. Trees attain in two years a height of three meters and a spread of two meters at Gainesville. Terminal growth of up to a meter is common on mature five-year-old trees. The first fruit ripen in early May at Gainesville or in about 75 to 80 days from full bloom. The fruit are uniformly medium large for an early ripening peach. Ripe fruit have 70 to 90 percentage of solid red skin color with no red pigment throughout the flesh or at the pit. The flower anthers are light red to yellow, a common characteristic of many standard peach and nectarine varieties.

BRIEF DESCRIPTION OF THE DRAWING

The accompanying drawing shows, in FIG. 1, the pedigree of the tree of this application through the ongoing planned breeding program conducted by the University of Florida, Gainesville, to result in the tree of this disclosure.

DETAILED DESCRIPTION OF VARIETY

Figure 1:
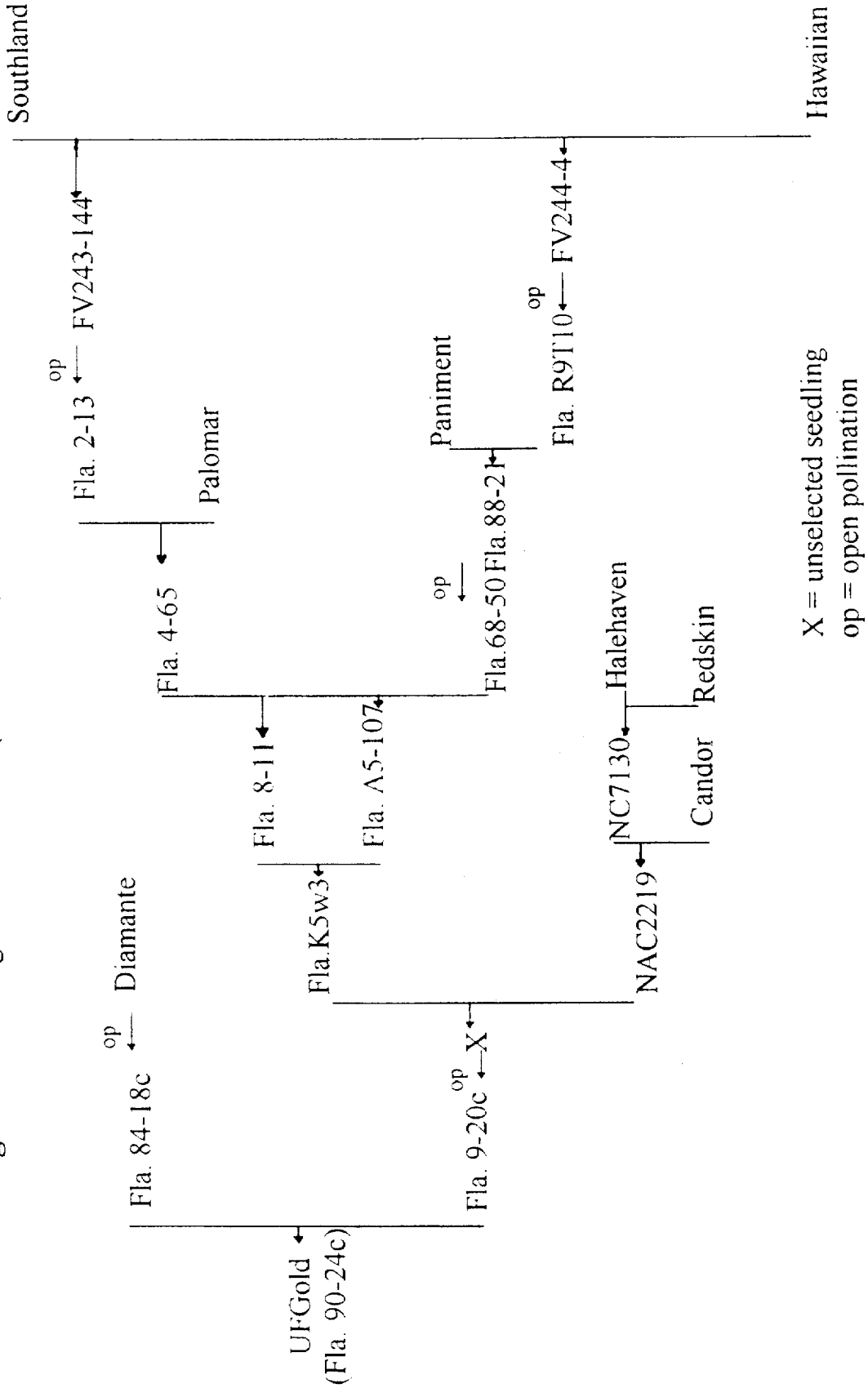
Figure 2:
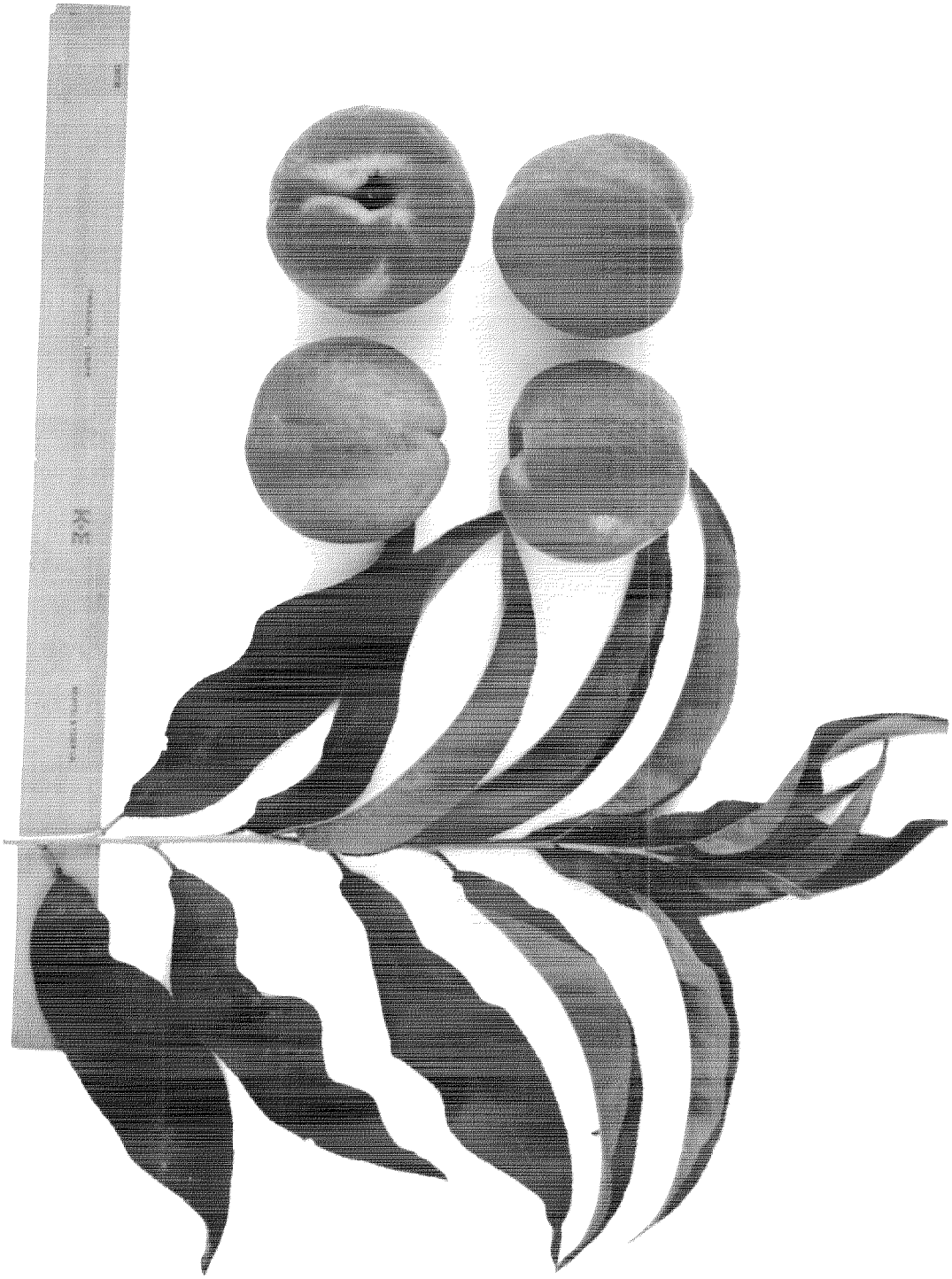
FIG. 2 is a color photographic showing of typical specimens of fruit, leaves and stem of the new variety as nearly true as it is reasonably possible to make in a color illustration of this type. The photograph shows the attractive shape and exterior coloration of four specimens of fruit beside a ruler in side view, stem end view, a blossom end view, and side view showing the characteristic suture. It also depicts the bark of new and fruiting wood, internode length, leaves, glands, leaf stems and axillary buds.

The tree flowers, and fruit may vary in slight detail due to variations in soil type, cultural practices, and climatic condition. The potential for commercial production of fresh fruit by UFGold is high, due to its attractive red skin, early ripening of good flavor, and exceptional firmness due to its non-melting flesh. The present botanical description is that of the variety grown under the ecological conditions prevailing near Gainesville, Fla. Colors are described from "The Pantone Book of Color" published by H. N. Abrams, Inc., N.Y. 1990.

Tree:

*Size.*—trees have been trained to an open vase form and are pruned in summer to keep center of vase open.

*Vigor.*—vigorous, must be summer and winter pruned to keep tree height restricted and to keep center of vase open.

*Density.*—Medium to dense.

*Form.*—semi-upright when pruned to vase shape.
*Bearer.*—regular, must be fruit thinned to avoid limb breakage and obtain larger fruit size.

Trunk:
*Size.*—Medium.
*Thickness.*—Medium.
*Texture.*—Medium smooth.
*Bark color.*—Older bark—lead gray (Pantone 17-1118).
*Lenticels.*—Numerous, small (2–4mm), and flatoral shape, with the center being Mineral yellow (Pantone 15-1046).

Branches:
*Size.*—Normal.
*Texture.*—relatively smooth, medium amount of lenticles.
*Color.*—New wood, Tarragon (Pantone 15-0326).

Leaves:
*Size.*—Medium; 15 to 19 cm length, including the petiole; 3 to 4 cm width. Measurements on vigorous upright shoots of summer growth.
*Thickness.*—Regular.
*Form.*—Lanceolate.
*Apex.*—Acute.
*Margin.*—Serrulate, slightly undulate.
*Base.*—Coneate.
*Surface.*—Glabrous.
*Color.*—Lower-Grasshopper (Pantone 18-0332); upper—Chive (Pantone 19-0323).
*Glands.*—Two to four small reniform glands mostly on lower leaf blade but occasionally on petiole, except up to six glands on vigorous shoots.
*Petiole.*—About 1 cm (0.7 to 1.1 cm).
*Stipules.*—Medium and early deciduous.

Flower buds:
*Abundance.*—Moderately high, mostly buds set fruit in absence of spring frosts.
*Size.*—Medium.
*Length.*—Medium.
*Shape.*—Plump, conic.
*Surface.*—Pubescent scales.

Flowers:
*Blossom period.*—With Flordaglo peach—average February 4–12th at Gainesville.
*Size.*—Large, showy.
*Color.*—Pink, darkening to pink red before abcising.
*Calyx cup.*—Medium small.
*Anthers.*—Light red to yellow, regular size.
*Pollen.*—Abundance and bright yellow (common to many varieties).
*Fertility.*—Self fertile.

Fruit:
*Maturity when described.*—Tree ripe, May 9, 1995 at Gainesville.
*Date of first picking.*—May 1, 1995 at Gainesville (normal).
*Size.*—Uniform, medium large (large size for early maturity at 110 to 125 grams). Average diameter axially-2¼ " (57 mm). Average length-2¼ " (57 mm).

Form:
*Longituduial section form.*—Round.
*Transverse section through diameter.*—Round.

Suture: Shallow and inconsipicuous.
Ventral surface: Rounded.
Base: Slightly retuse.
Cavity: Flaring circular.
*Depth.*—¼ to ⅜ inch (6 to 9 mm).
*Breath.*—5/32 inch (3 mm).

Skin:
*Thickness.*—Medium.
*Texture.*—Medium.
*Tenacity.*—Tenacious to flesh.
*Color.*—Red over 70 to 90% of skin. Ground color Tangerine (Pantone 15-1247). Red skin, Mars Red (Pantone 18-1655) to Cardinal Red (Pantone 18-1643) to Crimson (Pantone 19-1762).
*Tendency to crack.*—None observed.

Flesh:
*Ripens.*—Evenly.
*Texture.*—Firm, juicy, non-melting when fully ripe.
*Fibers.*—Very fine, tender, small.
*Aroma.*—High.
*Eating quality.*—Good, sweet, subacid.
*Juice.*—Abundant.
*Color.*—Yellow (Saffron-Patone 14-1064) with no redness throughout the flesh or at pit.
*Browning by oxidation.*—slight on soft ripe fruit.

Stone:
*Type.*—Clingstone, adhering to flesh even at softening.
*Size.*—Medium small; average length—30 mm, average width—23 mm.
*Color.*—Moderate brown (Pantone 13-1013) when freshly exposed.
*Form.*—Oblong.
*Base.*—Straight.
*Apex.*—Acute.
*Sides.*—Equal.
*Surface.*—Irregularly farrowed toward the ventral edge.
*Ridges.*—Jagged towed the base.
*Pit wall.*—3/16 to ¼ inch thick (5 to 6 mm).
*Tendency to split.*—none observed.

Use: Fresh; dessert.
Resistance to disease: High resistance to bacterial spot incited by *Xanthomonas campestris.*
Keeping quality: Good.
Shipping quality: Degree of firmness at harvest and firmness retained in refrigeration indicates fruit should be highy acceptable for shipping.

We claim:

1. A new and distinct variety of peach tree as illustrated and described, characterized by a low- chilling requirement and bearing moderately, early-ripening fruit with firm, yellow, non-melting flesh and high eating quality and an attractive high percentage red overcolor; and, fruit ripens in early May or with Flordaglo at Gainesville.

* * * * *

Figure 1. Parentage of 'UFGOLD' (Fla. 90-24c)